United States Patent
Bäuerlein (10) Patent No.: US 11,719,713 B2
(45) Date of Patent: Aug. 8, 2023

(54) GRIPPER FOR TEST SAMPLES, POSITIONING DEVICE FOR RAW SAMPLES, HANDLING SYSTEM FOR RAW SAMPLES AND TEST SAMPLES, AND TEST SYSTEM FOR VISCOELASTIC MATERIALS

(71) Applicant: MonTech System Solutions GmbH, Buchen (DE)

(72) Inventor: Ralf Bäuerlein, Buchen (DE)

(73) Assignee: MonTech System Solutions GmbH, Buchen (DE)

( * ) Notice: Subject to any disclaimer, the term of this patent is extended or adjusted under 35 U.S.C. 154(b) by 470 days.

(21) Appl. No.: 16/349,994

(22) PCT Filed: Nov. 17, 2017

(86) PCT No.: PCT/EP2017/079585
§ 371 (c)(1),
(2) Date: May 15, 2019

(87) PCT Pub. No.: WO2018/104030
PCT Pub. Date: Jun. 14, 2018

(65) Prior Publication Data
US 2019/0310272 A1    Oct. 10, 2019

(30) Foreign Application Priority Data
Dec. 6, 2016  (DE) .......................... 102016123585.7

(51) Int. Cl.
| | |
|---|---|
| *G01N 35/10* | (2006.01) |
| *G01N 35/00* | (2006.01) |
| *B01L 1/02* | (2006.01) |
| *B01L 9/00* | (2006.01) |
| *B25J 15/00* | (2006.01) |

(Continued)

(52) U.S. Cl.
CPC ............ *G01N 35/0099* (2013.01); *B01L 1/02* (2013.01); *B01L 9/00* (2013.01); *B25J 15/0066* (2013.01);
(Continued)

(58) Field of Classification Search
CPC ................................................. B25J 15/0071
See application file for complete search history.

(56) References Cited

U.S. PATENT DOCUMENTS

| | | | | |
|---|---|---|---|---|
| 4,805,949 A | * | 2/1989 | Conway ................. | B65G 47/90 271/18.3 |
| 2004/0194639 A1 | * | 10/2004 | Ilch ...................... | B25J 11/0045 99/450.6 |

FOREIGN PATENT DOCUMENTS

| | | |
|---|---|---|
| AT | 399835 B | 9/1993 |
| CN | 205270648 U | 6/2016 |

(Continued)

*Primary Examiner* — Paul S Hyun
(74) *Attorney, Agent, or Firm* — Michael Soderman (57) ABSTRACT

A skewer-type gripper for one-sidedly receiving a test sample positioned in a defined manner and still compressed by plungers in a punching device and consisting of viscoelastic materials with an upper side and an edge area. The gripper has a base and skewer-type means arranged in a plane therein, which can pierce into the edge area of the still compressed test sample parallel to the upper side. The skewer-type means are configured in such a way that the test sample can be received and held in a torque-proof manner by the skewer-type means. The gripper is configured and set up for horizontally receiving the test sample from a punching device, and the gripper or skewer-type means can be exposed to a feed force for this purpose.

2 Claims, 6 Drawing Sheets

(51) Int. Cl.
 *B25J 15/06* (2006.01)
 *G01N 33/44* (2006.01)
 *B25J 15/02* (2006.01)

(52) U.S. Cl.
 CPC ....... *B25J 15/0071* (2013.01); *B25J 15/0206* (2013.01); *B25J 15/0616* (2013.01); *G01N 33/442* (2013.01); *B01L 2200/087* (2013.01); *B01L 2300/10* (2013.01)

(56) References Cited

FOREIGN PATENT DOCUMENTS

| | | | |
|---|---|---|---|
| DE | 3040197 | A1 | 5/1981 |
| DE | 000008417777 | U1 | 1/1986 |
| DE | 8417777 | U1 | 1/1986 |
| DE | 4442839 | A1 | 6/1995 |
| DE | 20212963 | U1 | 1/2003 |
| DE | 102004020959 | A1 | 2/2005 |
| DE | 102007031847 | B3 | 10/2008 |
| DE | 202012101859 | U1 | 5/2013 |
| DE | 102012018438 | A1 | 3/2014 |
| DE | 102014226160 | A1 | 6/2016 |
| DE | 202016103770 | U1 | 10/2016 |
| EP | 1306660 | A2 | 5/2003 |
| EP | 2769803 | A2 | 8/2014 |
| JP | S62074989 | U | 5/1987 |
| JP | H04166077 | A | 6/1992 |
| JP | H636794 | U | 5/1994 |
| JP | H08198444 | A | 8/1996 |
| JP | 2003194707 | A | 7/2003 |

\* cited by examiner

Prior Art

GRIPPER FOR TEST SAMPLES, POSITIONING DEVICE FOR RAW SAMPLES, HANDLING SYSTEM FOR RAW SAMPLES AND TEST SAMPLES, AND TEST SYSTEM FOR VISCOELASTIC MATERIALS

CROSS REFERENCE TO RELATED APPLICATIONS

This application is the U.S. national stage of International Application No. PCT/EP2017/079585, filed on Nov. 17, 2017. The international application claims the priority of DE 102016123585.7 filed on Dec. 6, 2016; all applications are incorporated by reference herein in their entirety.

BACKGROUND

The invention relates to a gripper for handling test samples comprised of viscoelastic materials, a positioning device for raw samples comprised of viscoelastic materials, a handling device for raw samples and test samples and a test system for testing materials with viscoelastic properties, such as plastics, including rubber mixtures, abrasive materials, adhesives and silicones.

Material testing is used for quality control purposes, and performed during various manufacturing stages, such as material production, the purchase of intermediate and end products, and research and development.

The most well-known materials with viscoelastic properties are plastics. They consist of organic macromolecules, which are fabricated either by converting natural products, such as rubber, or artificially by synthesizing low-molecular organic compounds. Low-molecular building blocks are here chained into macromolecules while supplying energy, and usually mixed with additives. Depending on the composition and mixtures, this yields different types of plastics, which can be differentiated based upon their behavior into thermoplastics, thermosets and elastomers. Thermoplastics, for example celluloid, can be shaped time and again by supplying energy, and are processed during an injection molding or extrusion process, for example. Thermosets irreversibly cure at room temperature and form brittle bodies, which are typically used as housings or body parts processed in casting or molding processes. Elastomers are elastically deformable at a normal temperature, meaning that they assume their original shape again after expansion. Natural rubber can be turned into hard or soft rubber through treatment with sulfur or vulcanization, but rubber can also be synthetically manufactured. Rubber mixtures arise by adding additional materials. Rubber is a synonym for rubber mixtures. Abrasive materials consist of rubber mixed with sand, and are used as brake linings, for example. As a rule, adhesives have synthetic resins or rubbers as the base material. Silicones are compounds consisting of inorganic silicon and organic residues, which in viscoelastic form are known as silicone rubber, silicone elastomers or also silicone resin.

Depending on their composition, the aforementioned materials have their specific characteristics, which relate in particular to flowability, temperature resistance, wear, hardness, density, elasticity, viscosity, vulcanization capacity, processability, shelf life, ozone resistance, dispersion, fatigue, abrasion and process capability, but also to the service life. These values can be determined with corresponding material testing machines.

In material production, material testing serves to check the materials for their processing suitability after the mixing process. In order to test the processing characteristics, the testing machines simulate the manufacturing steps with the respective material, which is why the consistency of the material to be tested corresponds to the consistency at the time of processing. This is for purposes of processability in the injection, pressing and molding tools having a corresponding viscosity, for example, which are partially gelatinous and still have an incompletely developed elasticity, which results in an elevated stickiness that makes handling difficult. Raw samples are initially taken from the rolled out material for test purposes, so as that several test samples of a material batch can be fabricated from them. The size of the raw samples can vary, and typically ranges from 40 to 120 millimeters, while the thickness ranges from 5 to 18 millimeters. The size of the test samples punched out of these raw samples can also vary, and typically ranges from 30 to 50 millimeters, while their thickness is determined by that of the raw sample.

In conjunction with material production, the time factor is of crucial importance for material testing, i.e., the timeframe after manufacturing a finished batch within which a test result is present. For example, rubber mixtures are prepared in batches of 200 to 500 kilograms each over a short time unit of approx. two to four minutes during exposure to heat, for example in mixing systems. When still about 70-80° C. hot, the mixtures are then immediately rolled into webs, the so-called films. Since the mass is still sticky at this point in time, the material web is coated with an anti-adhesive agent (release agent, e.g., talcum) before being cooled in the film cooling system during further transport.

For test purposes, a raw sample is taken from such a material web by an operator, in some cases by a raw sample cutting device. The latter is most often freed of the release agent layer still in a washing device, as a result of which a certain cooling takes place. The raw sample is then freed of the washing solution through drying, for example with compressed air, and in an ensuing step is fed to the punching device, for example a volume punch, in which the actual test samples are punched out. To this end, the raw sample is compressed by a compression plunger coming from above onto a fixed plunger, after which a cylindrical punch iron guided around the fixed plunger is guided toward the top through the material, so that a test sample arises in the area of the plunger surface. During the punching process, a volume punch ensures that the test sample always has the same material volume. Removal from the punching device has to date taken place manually after opening the compression plunger. The adhesive effect of the material can result in the test sample becoming stuck on both compression surfaces. Therefore, removing the test sample is a cumbersome activity, which requires caution and skill.

The test samples are fed to the testing machines at a temperature ranging from 25 to 100° C. The latter check them to see whether the respective material mixture corresponds to the quality requirements.

The testing machines normally stand in a test laboratory, so as to ensure defined test conditions. A specific spatial distance must thus be overcome for fitting the testing machines. For this reason, it can take a good thirty minutes starting from when the raw sample is removed for the testing machines to be fitted with test samples during conventional manual handling. The time window from raw sample removal to test sample measurement determines the possibly produced scrap quantity, which can easily measure several thousand kilograms. This is an important cost factor for the producer. Fluctuations in time progression, which depend on the skill of the operator, can also detract from the reliability of measuring results.

Automated handling has thus far failed because the aforementioned materials could not be handled in the hot, sticky state using conventional automation technology. Each mechanical access with conventional gripping technology would involve the danger of becoming stuck to the gripping element. This runs counter to a reliable, frictionless handling and precise positioning of the test samples.

DE 10 2007 031 847 B3 discloses a gripping device for an industrial robot for grasping and placing flexible objects, such as meat, vegetables or small fish. This gripping device has a combination of two suction cups in a contact surface located above the object and a gripper pair lying in between, wherein the gripper pair additionally grips the side of the object already grasped with the suction cups. This gripper is unsuitable for handling flat, dimensionally unstable and sticky objects.

DE 10 2012 018 438 A1 describes a handling device with a manipulator located on a robot arm for planar objects, such as films, mats or thin plates. Several suction cups are used to remove individual layers, e.g., damping mats, from a supply cartridge located directly on the robot arm, and place them at the assembly site. In particular for assembling several such objects within a hollow space, such as an automobile, this device makes it possible to assemble several of these objects one after the other, without having to move the robot arm out of the hollow space. This device is not suitable for handling raw samples and test samples in material testing, since raw samples and test samples cannot be placed and handled in layers.

Further known are needle grippers for gripping and transporting porous, textile or soft objects, such as fabric layers. Let DE 20 2016 103 770 U1 be mentioned as an example here, which further develops such a needle gripper. The known needle grippers are provided with needles that can be moved out of a base in pairs, diverging and/or converging from above into an object, so that the object is held while lifting the needles that act like barbs, piercing in an opposite angular position. Such a needle gripper is not suitable for handling viscous and sticky raw samples or test samples, since needles piercing into a raw sample or test sample at an inclination from above would not encounter enough resistance in the soft, possibly still gelatinous mass without sufficient shape stability. There would be a danger of slippage, and the reliable positioning of a test sample is not possible. This gripper is unsuitable in particular for removing sticky test samples from a punch. This is because the working range of a punch as a rule does not allow any access from above. Either the punch iron with the ejector is above the test sample, or the compression plunger is, given volume punches.

Further known are grippers with needle elements that can be moved toward each other in pairs. For example, AT 399 835 B describes a gripper with two gripper fingers that can be controllably moved toward each other, on which several gripping needles are arranged. These gripping needles are used for point-wise placement, and thus also for distributing the holding forces onto the body to be held, such as microtiter plates, and are arranged on a rocker to offset possible irregularities on the surface. It is intended to ensure a secure hold even given low holding forces, while at the same time preventing damage to the surface. For this reason, the needles are not designed for piercing, but for point-wise placement on a solid body, and the gripper as a whole is not suitable for skewering and handling soft, sticky test samples.

DE 000008417777U1 describes a device for removing back-cut soft foam parts from their molds, which comprises a gripper device with two needle-fitted jaws that can be moved against each other. This gripper is also only suitable for objects that have a certain structural strength in their body. Such a gripper is not suitable for handling sticky test samples, i.e., ones that are instable in particular as regards their physical shape.

SUMMARY

The invention involves a skewer-type gripper for one-sidedly receiving a test sample positioned in a defined manner and still compressed by plungers in a punching device and consisting of viscoelastic materials with an upper side and an edge area. The gripper has a base and skewer-type means arranged in a plane therein, which can pierce into the edge area of the still compressed test sample parallel to the upper side. The skewer-type means are configured in such a way that the test sample can be received and held in a torque-proof manner by the skewer-type means. The gripper is configured and set up for horizontally receiving the test sample from a punching device, and the gripper or skewer-type means can be exposed to a feed force for this purpose.

DETAILED DESCRIPTION

Therefore, the object of the invention is to provide elements for an automatic handling of raw samples and test samples during the material testing of viscoelastic materials. One central task involves a gripper for handling sticky test samples made out of viscoelastic materials, which have a planar surface and a lateral edge surface, hereinafter referred to as edge area.

This object is achieved with a skewer-type gripper, which has a base and skewer-type means arranged therein, which can pierce the edge region of a test sample parallel to the upper face and are designed such that the test sample can be held by the skewer-type means in a rotationally fixed manner. The skewer-type means exert a loadbearing effect that counteracts gravity with respect to the material lying above the skewer-type means on the one hand, and the frictional forces acting between the piercing skewer-type means and test sample further ensure a secure hold. The rotational resistance is achieved by a non-rotationally symmetrical configuration of the skewer-type means, specifically by a horizontal expansion parallel to the upper side of the test sample, which offers resistance to a rotation by the test sample around the skewer-type means. Such a gripper makes it possible to securely grip the test sample from only one side. What this means is that the gripping movement of the skewer-type gripper takes place in one direction, without requiring any interaction with a second gripping element. Because the skewer-type means penetrate into the edge area of the test sample on a plane parallel to its upper side in the process, the skewer-type gripper can additionally already be used with the test sample still fixed in the punch by the compressive force. This permits a defined, positioned accommodation and the lifting of test samples sticking to the stamping puncher, which enables a defined, positioned relaying of the test sample. The hollow spaces in the material created by skewering the test sample close either because enough viscosity is still present, or later as in the case with hard rubber in the testing machine, which itself acts on the test sample with high forces. They do not disturb the testing process. In particular, this skewer-type gripper according to the invention makes it possible to realize this most difficult part of handling test samples that are still hot and sticky. This provides the opportunity of automating the handling of viscoelastic test samples while testing materials, and beyond that the entire preparation and testing process.

In one expedient configuration, the skewer-type means are configured as needles arranged in parallel. Due to the minimized resistance, the latter pierce especially well. Parallel guided needles can be fixedly arranged on the gripper. In the case of movable needles. They simplify the feed motion, since only one drive is needed for this purpose.

An advantageous further development provides for a stripping device, with which a skewered test sample can be pushed by the skewer-type means, wherein the stripping device has a front surface arranged in front of the base with a recess through which the skewer-type means can pass, and wherein the front surface and skewer-type means are designed so that they can move relative to each other, and arranged in such a way that, for accommodating a test sample, the skewer-type means in a gripping position can protrude through the recess in the front surface, and are masked by the front surface after the test sample has been stripped.

The stripping device arranged directly on the skewer-type gripper allows a positioned placement on difficultly accessible positions without additional tools or aids. Another advantageous effect of the stripping device is that the front surface masks the skewer-type means in the rest position, and prevents accidents or collisions between the skewer-type means and other devices or individuals.

Possible embodiment variants provide that either the skewer-type means or front surface be immovable in design. If the front surface is immovable, it is located near the base. The gripper can then be moved toward the accommodating position in an especially space-saving manner, and only deploy the skewer-type means on site. Deployment can here take place both before piercing, so that the feed force emanates from the entire gripper, or the piercing means are introduced into the test sample from the gripper positioned directly in front of the test sample, so that the skewer-type means must be exposed to the feed force.

An advantageous further development of the skewer-type gripper provides that the skewer-type means have at least one hollow needle. Hollow needles can be pressurized with compressed air, thereby enabling support for the mechanical stripping of sticky test samples.

The object of providing elements for the automated handling of raw samples and test samples during the material testing of viscoelastic materials is further achieved with a multifunctional gripper, which comprises
- a first effector with gripping jaws that can be moved toward each other in pairs for receiving and handling, by moving, positioning and securing, a raw sample before and while punching the test sample,
- a second effector with a skewer-type gripper according to the invention for receiving and handling by transferring test samples after punching,
- a third effector with suction means for handling, by transferring and positioning, a test sample,
- a fourth effector with suction means for handling by transferring a raw sample, wherein each of the effectors is arranged and designed so that it can be controlled in terms of its position, its position relative to the raw sample or test sample, its alignment, contact force and movement.

Such a multifunctional gripper can be used in conjunction with a robot arm, which can perform all handling processes with one multiaxial arm instead of four separate movement axes. This allows a space-saving and especially efficient handling. The first effector here serves to receive the raw sample, which can be fed either manually or automatically, and after processing steps have been handled, to move it into the area of the punching device, as well as to intermediately store it after the punching process for further deposition. For example, the preparation steps include washing and drying the raw sample, but also involve introducing edge cuts between the edge and punching area, which after punching make it possible to separate the raw sample from the test sample still fixed in the punch. In the punching device, a compression plunger compresses the raw sample in the punching area against an abutment surface, before the punching iron punches out a test sample in the opposite direction. Thanks to the edge cuts located in the raw sample, the first effector holding the raw sample can pull the raw sample out of the punching device around a compressed test body. The opposing gripping jaws can be used to grab both sides of the raw sample in an edge area in such a way that the remaining area remains accessible for punching out test samples. Gripping jaws are readily controllable, thereby ensuring that the necessary traction is exerted. The gripping jaw pair of the first effector here fixedly and reliably holds the raw sample, so that its position within the gripper does not change during exposure to all mechanical loads.

The skewer-type gripper on the second effector can be positioned in front of the test sample, and the latter can be driven with an actuating power laterally into the test sample against the friction in the test sample and compressive force of the punching device. After removing the compression plunger, the test sample can be lifted up. The test sample is positively connected with the skewer-type means via piercing, which allows a reliable lifting and positioning. In addition, the test sample is reliably held by the frictional forces acting between the test sample and skewer-type means. The mode of action and advantages of the gripper according to the invention for handling a test sample have already been extensively described.

The third effector in the form of a suction gripper serves to receive the test sample from the intermediate storage and to position the test sample for supply to the test unit after it has been stripped by the second effector in an intermediate storage. The holding force of a suction gripper is sufficient for this type of handling, which essentially only has to withstand the gravitational force of the test sample. The latter permits a simple receiving and deposition at defined positions.

The fourth effector is likewise configured like a suction gripper, and used in the final handling of raw samples after the punching process has ended, i.e., after the first effector has deposited the completely processed and possibly still labeled raw sample in an intermediate storage. The raw sample is there received by the fourth effector and placed in a container for final storage (waste, archiving, follow-up inspection). Exact positioning is usually not required for this purpose; however, the fourth effector must have a stronger configuration than the third effector given the larger dimensions of the raw sample relative to the test sample. This fourth effector is also expedient for increasing the parallelization of the operations.

An advantageous embodiment provides that the gripping jaws of the first effector have a marginal recess in the gripping area, making them at least partially divided into two. This configuration allows an interaction with an embodiment of the positioning device described below, with which raw samples can be received at a defined position with the first effector of the multifunctional gripper.

Another partial objective of the invention is to provide means that allow the positioning of a viscoelastic raw sample for a handling system.

This partial object is achieved with a positioning device, comprising:
- a sliding surface with a longitudinal alignment Y and transverse alignment X, wherein the sliding surface has a receiving side opposed in the longitudinal alignment Y by a deposition side,
- wherein the sliding surface has an inclination from the receiving side to the deposition side, which can prompt the supplied raw sample to move along the direction of inclination through exposure to gravity,
- and wherein edge elements as guides for the raw sample during movement on the sliding surface during operation are arranged on both sides along the sliding surface, which converge in the direction of inclination, so as to position the raw sample within the transverse direction X during operation,
- and wherein catching means are provided on the deposition side, which catch the raw sample during operation upon reaching the deposition side in a defined position within the longitudinal alignment Y,
- and wherein the catching means have edge elements as well as a pin or hook, which protrudes from the plane of the sliding surface at the deposition end between the edge elements,
- and wherein the sliding surface has cavities on both sides of the pin or hook as engagement areas for gripping jaws as well as rollers, which are rotatably mounted in the direction of inclination.

The sliding surface downwardly inclined toward the deposition side causes a raw sample supplied on the receiving side to slide toward the deposition side through exposure to gravity. At the same time, the edge elements provide for a reliable guiding on the sliding surface. Their tapering yields a positioning of the raw sample within the transverse alignment X of the sliding surface. The raw sample is positioned in the longitudinal alignment by the catching means, which are arranged in the deposition area. As a result, the raw sample is held ready within the positioning device in exactly an X-Y position for reception by the handling system, and it becomes unnecessary to acquire the position by means of a sensor array or other means and control the receiving gripper accordingly. The configuration of the catching means provide that they be formed by the edge elements. To this end, the distance between the edge elements at the end of the tapering must be dimensioned in such a way as to be smaller than the diameter of the raw samples. The raw sample can then be caught by the edge elements in the deposition area. The pin or hook that protrudes from the sliding surface at the deposition end between the edge elements permits a reliable positioning of raw samples whose radius is smaller than the distance between the edge elements, since they are centered at a defined position when caught and held ready for removal. In this configuration, raw samples of varying size can be reliably positioned without retrofitting. The two recesses on the deposition side serve as an engagement area for gripping jaws, in particular paired or two-part ones. This allows simple and reliable access for removing the raw sample from the positioning device from its defined position, wherein the pin or hook can serve as a guide for the gripping jaws. The configuration of the sliding surface with rollers rotatably mounted in the direction of inclination reduces the friction between the raw sample and sliding surface, which could result in undesired deposits on the surface, and hence a reduction in sliding capability during the course of operation. This ensures a durable sliding capability of the raw samples on the sliding surface.

The object of the invention is further to provide a handling system that allows an automatic handling of raw samples and test samples punched from them comprised of viscous materials of the kind required for material testing.

This is enabled with a handling system comprising:
- a first effector with gripping jaws that can be moved toward each other in pairs for receiving and handling, by moving, positioning and securing, a raw sample before and while punching the test sample,
- a second effector with a skewer-type gripper according to the invention for receiving and handling by transferring test samples after punching,
- a third effector with suction means for handling, by transferring and positioning, a test sample,
- a fourth effector with suction means for handling by transferring a raw sample, wherein each of the effectors is arranged and designed so that it can be controlled in terms of its position, its position relative to the raw sample or test sample, its alignment, contact force and movement, and the effectors are arranged on a multifunctional gripper, and the latter on a robot arm, and further comprising
  - control means for the effectors, so as to control the handling of raw samples supplied to the system as well as the test samples punched from them according to the previously mentioned functions while preparing and implementing the material test.

The functions of the effectors correspond to those of the multifunctional gripper already described before, except that they can also be located on axes to be controlled independently. This handling system permits the completely automated handling of raw samples and test samples consisting of soft, sticky materials. As a consequence, material tests of such materials can be performed significantly faster and at a constant quality during production. The fact that the effectors are arranged on a robot arm by means of a multifunctional gripper permits a more effective use. In this case, all four effectors are arranged on the multifunctional gripper in such a way that the robot arm can put each effector to use separately. As a result, only one robot arm must be moved and controlled, which saves on space and simplifies the processes.

The object of the invention is further to provide a system for fully automated material testing for materials with viscoelastic properties.

This is achieved with a test system comprising:
- a handling system according to the invention,
- a punching device for punching test samples out of a raw sample,
- a test unit with at least one testing machine for implementing material tests on test samples,
- a positioning device for supplied raw samples,
wherein the control means are designed so as to control the effectors in such a way during operation that a raw sample is supplied to the punching device, punched out test samples are removed from the punching device and supplied to the test unit, and that the test results can be acquired, analyzed, displayed and passed along.

Incorporating a positioning device enables an automated supply to the test system, since the test system can receive the test sample in a defined position, and feed it to the additional stations in a defined manner. The handling device can implement the required operations with the punching device in a fully automated manner, and feed the generated test samples to the test unit, also in an automated manner. The test unit can contain one or more testing machines, so that a test sample can be fed to a specific testing machine as needed. Since the testing machines are modularly arranged in the test unit, the test unit can contain correspondingly required testing machines for the various parameters. The control means can process and analyze the collected results, and relay the test results either to a corresponding output unit or in some other way.

An advantageous embodiment of the system provides that a storage device be provided for intermediately storing punched test samples. This makes it possible to achieve a stronger parallelization for the processes. In principle, tests can last one to thirty minutes, even though most tests only last a few minutes in practice. If the test unit is occupied, the test samples can be fabricated out of raw samples unimpeded, and the prepared test samples can be intermediately stored in a type of buffer station. To ensure secure positioning, the latter is advantageously equipped with at least one trough, into which a test sample can be correctly deposited, so as to permit a reliable, defined retrieval by the third effector. This ensures that the position of the test sample will not be inadvertently changed during intermediate storage. The at least one trough has an elevated edge area, which extends over part of the periphery of the trough, and on which the skewer-type gripper according to the invention can reliably and gently strip the skewered test sample as the second effector. The round fit of the edge area enables an efficient stripping. The number of troughs must be oriented to the equipment and performance of the system.

The system is further preferably configured in such a way that it can be coupled with a material production line having a mixing device and a controller, wherein the control means of the test system can interact with the control means of the production line with regard to the test results of the test unit in such a way that the mixing device can be controlled as a function of the analysis results of the test system control unit. The coupling can take place via an interposed conveying path, or also through direct connection. It is crucial here not just that the mechanical elements interact, so that the raw samples are relayed to the test system in a fully automated manner, but also that the control means of the test system interact with the control means of the mixing system in such a way that the mixing ratios can be modified depending on the test result. As soon as the tests in the test system show that a parameter has not been satisfied, the mixing device can respond by adjusting the composition for the next batch. As a consequence, material losses can be minimized, making it possible to achieve a more efficient material production.

An advantageous embodiment provides that the test system be encased airtight by a housing, in which a device for generating overpressure is provided. Handling devices are provided with protective housings for safety reasons. Making such a housing airtight enables the achievement of defined test conditions, similar to those in a conventional test laboratory. This makes it possible to avoid impairment caused by dust, temperature and moisture fluctuations. The device for generating an overpressure, for example in the form of an air conditioning system, can be used to generate an overpressure in the housing that reliably prevents the penetration of dust particles from the environment, even if the door to the housing must be opened, for example. Precisely because the test system can stand in direct proximity to the production facility, polluted air must be expected, so that the pollution can be countered with this embodiment. The air conditioning system can further be used to set defined temperatures, and hence defined test conditions.

Equipping this test system with the efficient variant of the handling system in the form of the robot arm with the four effectors connected in a multifunctional element yields a most effective, autonomously operating and self-contained test cell, which can be coupled to material production as a module and interact with the latter, without there being any quality fluctuations relative to the test samples or major time delays up until the test.

BRIEF DESCRIPTION OF THE DRAWINGS

The invention will be explained in more detail based on the drawing. Shown on.

DETAILED DESCRIPTION OF THE PREFERRED EMBODIMENTS

Figure 5A:
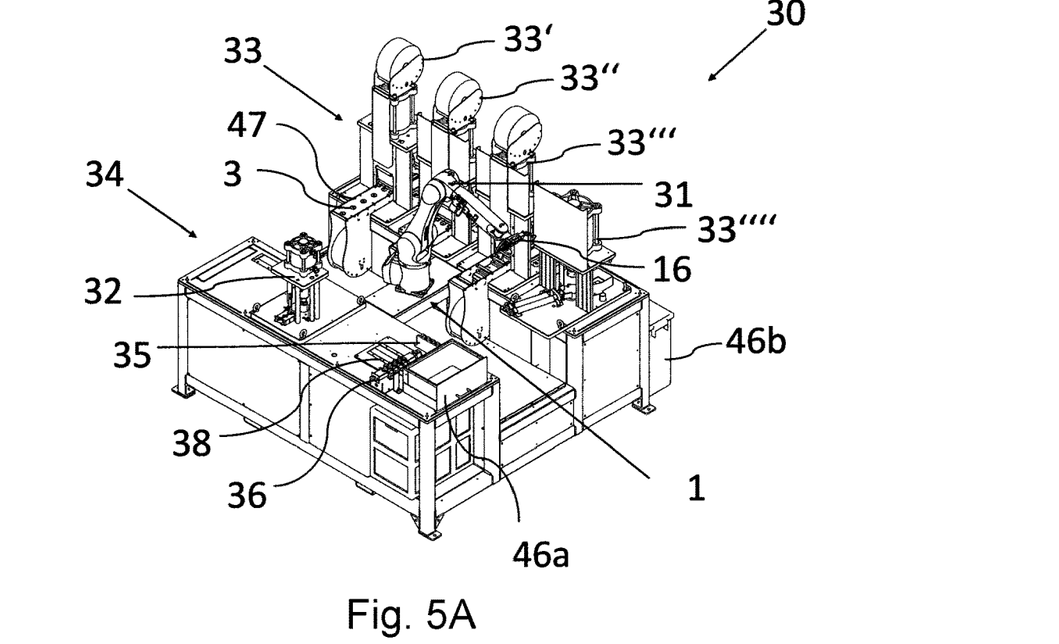
FIG. 5A, 5B is the test system according to the invention in another exemplary embodiment from two different perspectives.
Figure 5B:
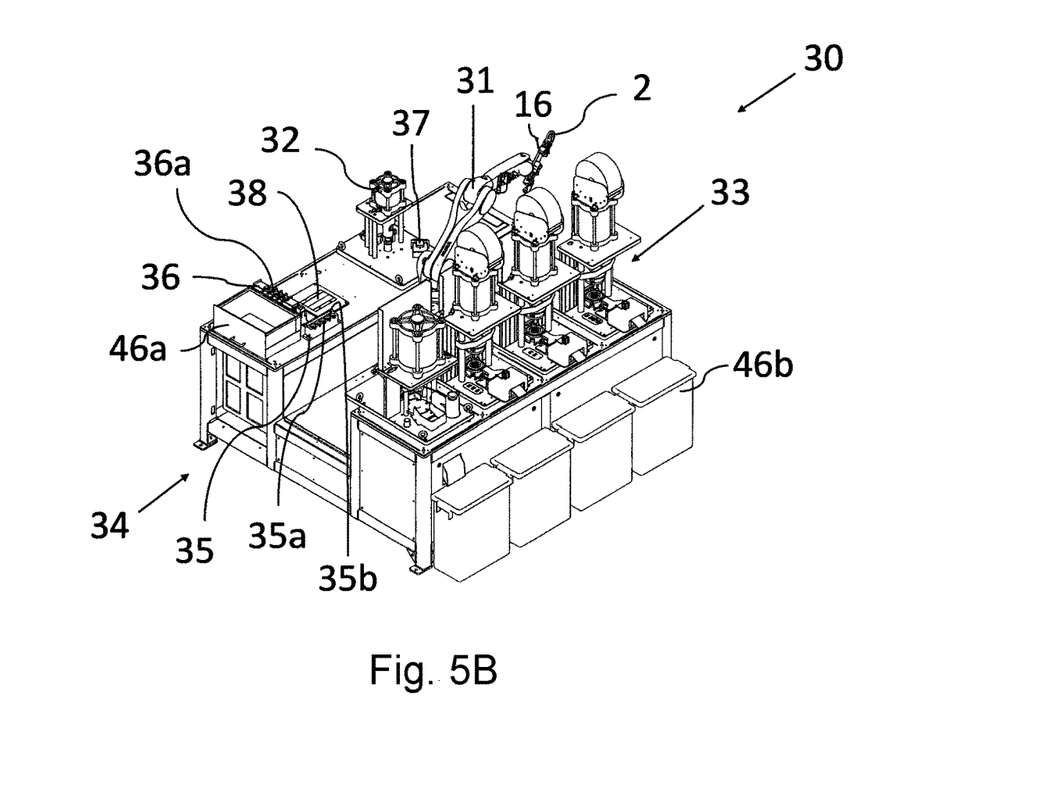
Figure 6A:
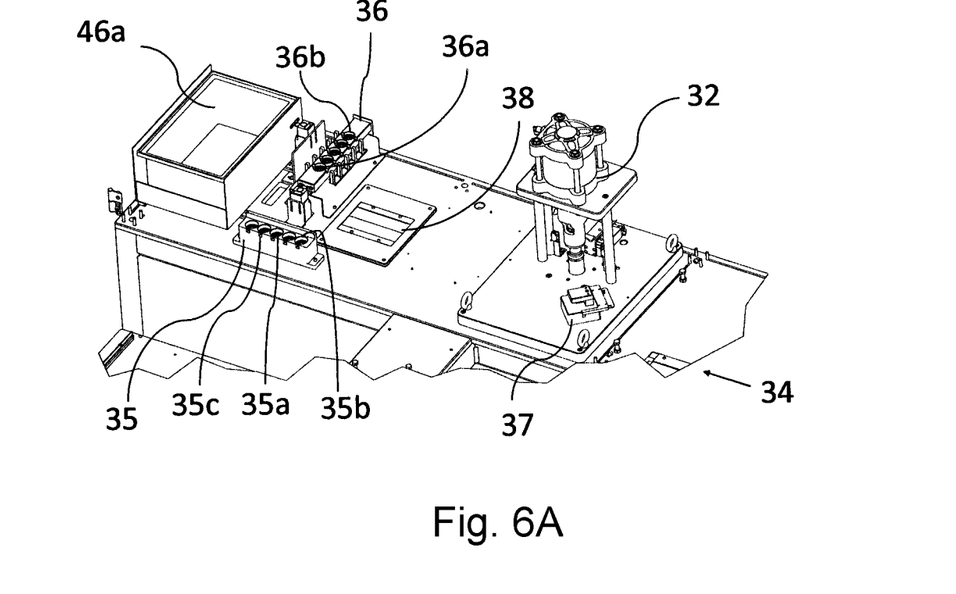
FIG. 6A is a cutout from FIG. 5b in detail (punching device and edge cutting device)
Figure 6B:
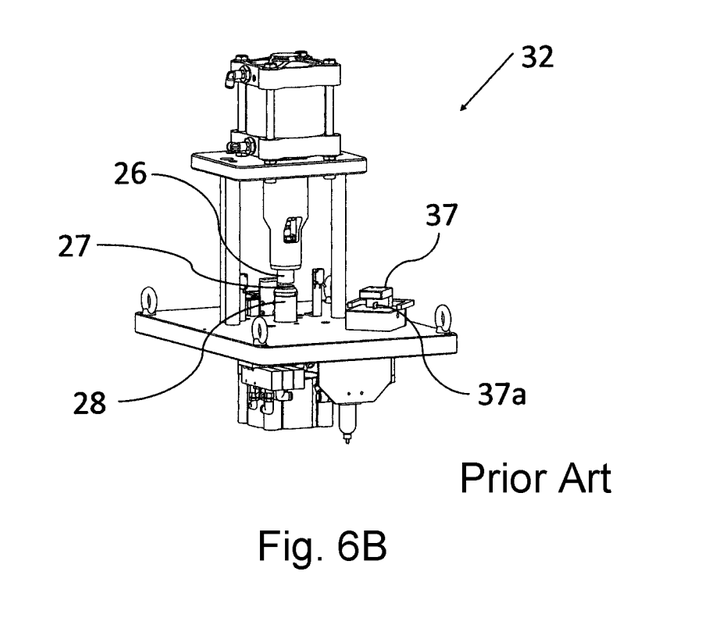
FIG. 6B is another cutout of 5b in detail (storage device according to the invention)

FIG. 1 shows an exemplary embodiment of a multifunctional gripper 16 according to the invention with four effectors 4, 6, 13, 14 in the inoperative position, of the kind that can be used in a handling system 1 of a test system 30 (see FIG. 6a, 6b). Such a multifunctional gripper 16 is intended to be fastened to a linear system (see FIG. 3) or to a robot arm 31 (see FIG. 5a, 5b), and, by correspondingly positioning and orienting as well as activating the effectors 4, 6, 13, 14, to perform all required handling operations on raw samples 2 (not shown) and test samples (not shown) in preparing and implementing material tests. However, the skewer-type gripper 6 can just as well be used independently.

Figure 1A:
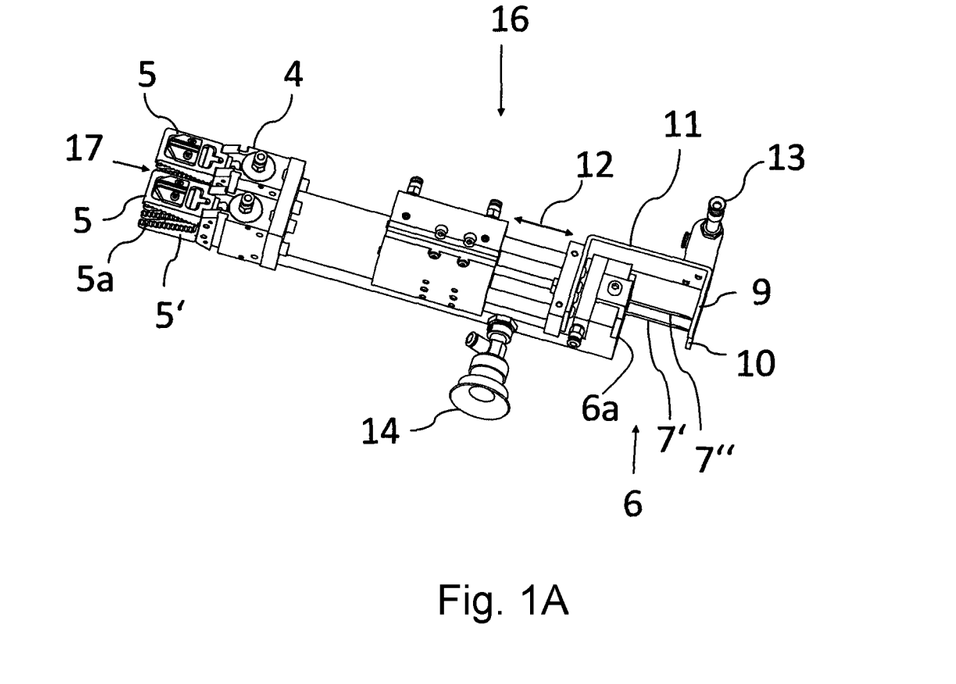
FIG. 1A is the skewer-type gripper for test samples and other partial elements of the handling machine according to the invention in an exemplary embodiment, FIG. 1B, C, D are alternative exemplary embodiments of the skewer-type means as a schematic sketch.

The first effector 4 is here configured as a double gripping jaw pair 5, 5', and used for handling a raw sample 2 (not shown) once received in the handling system 1 (see FIG. 5a), and intermediately storing it after the punching process. The skewer-type gripper 6 according to the invention as a second effector 6 is used for handling a punched test sample 3 (not shown) during removal from the punching device 32 (see FIG. 6a) up to the intermediate storage. The third effector 13 designed as a suction gripper 13 is used for receiving a test sample 3 (not shown) from the intermediate storage and feeding it to the test unit 33 (see FIG. 5a, 5b).

The fourth effector 14 likewise designed as a suction gripper 14 is used for again receiving the deposited raw sample 2 for final handling.

The dual or two-part gripping jaws (5, 5') are here spaced apart from each other in such a way as to form a recess 17. The same effect was achieved in one-part gripping jaws 5, 5' by having the gripping jaws 5, 5' have a terminal recess over a portion of their gripping area. This configuration allows an interaction with the positioning device 20 described on FIG. 4a, 4b. The surfaces of the gripping jaws 5, 5' have a fluting 5a, which upon coming into contact with the soft raw sample 2 presses into the latter. If the fluting 5a has a saw-toothed contour, the holding force in one direction can be increased. The saw-toothed contour is best arranged in such a way as to strengthen the holding force against removing the raw sample 2. This makes it easier to receive the raw sample, and the feed force required of the gripping jaws 5, 5' for a secure hold can be reduced. In order to deposit the raw samples 2 that adhere due to their stickiness, these can either be shaken or stripped off after opening the gripping jaws 5, 5'. This is because the processed raw samples 2 no longer have to be exactly positioned, but are collected in storage containers 46a (see 5a).

The skewer-type gripper 6 according to the invention as the second effector 6 here has two parallel-arranged needles 7', 7" anchored perpendicularly in the base 6a as piercing means 7. As a rule, such needles 7', 7" for conventional test samples 3 have a diameter of 1.6 to 1.8 millimeters. They can be designed as hollow needles 7', 7", as discernible here in outlines, so as to support the mechanical stripping of the test samples 3 through exposure to compressed air. Given immovably configured needles 7', 7", the stripping device 9, 10 is here configured as an adjustable front surface 9 with a recess 10. The front surface is here connected by an actuator 11 with the skewer-type gripper 6, and is located in a position that masks the needles 7', 7". The double arrow 12 represents the displacement path of the actuator 11.

The actuator 11 is used to move the front surface toward the base 6a, so that the needles 7', 7" protrude through the recess 10 (here only discernible in outlines, see also FIG. 2), and can be made to pierce into the edge area 3a of a test sample 3 (see FIG. 2) with a corresponding feed force. The required feed force can lie between a few grams for silicones and up to eight kilograms for hard rubber.

The suction gripper 13 for handling the test sample 3 while feeding it to the test unit 33 is used as the third effector 13 (see FIG. 5a, 5b). After the testing process, the test samples 3 can be removed directly from the testing machines out of the system, for example into a storage container. While the suction gripper 13 is here designed as a vacuum cup and has less holding force than the skewer-type gripper 6, it is sufficient for the respective handling steps, since the test sample 3 need only be received, transported and positioned against the force of gravity. The suction device can also be configured as a suction mount or airflow cup.

The same holds true for the fourth suction gripper effector 14, here also shown as a vacuum cup, which is used to further handle the raw sample 2 once the punching process has ended. It must only have a correspondingly higher holding force than the third effector 13, since raw samples 2 are larger than test samples 3. After the punching process, during which up to five test samples 3 are punched out of a raw sample 2 one after the other, the raw sample 2 is taken by the first effector 4 into an intermediate storage, from where it is received by the fourth effector 14, and in order to be removed from the system can be moved into a corresponding repository 46a (not shown, see FIGS. 5a and 5b), for which exact positioning is no longer required. For example, such a repository 46a can be a storage container 46a to be taken to waste disposal or the archive.

Depending on the arrangement of the effectors 4, 6, 13, 14 on the multifunctional gripper 16, the robot arm 31 (not shown, see FIG. 5a, 5b) must be movably configured and controllable. The effectors 4, 6, 13, 14 are best aligned in various directions and terminally arranged, so as to ensure a good engagement in machine areas.

Figure 1B:
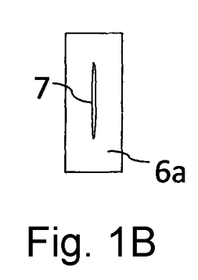
Figure 1C:
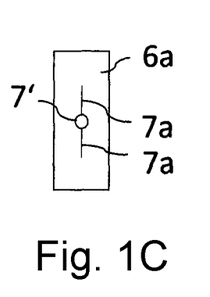
Figure 1D:
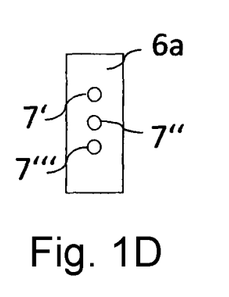

FIGS. 1b, 1c and 1d show alternative possible embodiments of the piercing means 7, in a top view on the base 6a. The piercing means 7 are configured as a flat oval on FIG. 1b, which here is completely hollow in design. This contour ensures the torque-proof hold. FIG. 1c presents a central, rotational symmetrical hollow needle 7' with laterally arranged ribs 7a as the piercing means 7, wherein the ribs 7a ensure the torque-proof hold. FIG. 1d depicts the skewer-type means 7 configured as three parallel needles 7', 7", 7''', which here are also designed as hollow needles. Such a multiple arrangement is necessary when using rotationally symmetrical needles 7', in order to ensure the torsional strength of the hold. If the needles are immovably arranged, they must also be arranged in parallel. If movably arranged in the base 6a, they can also converge or diverge slightly. It is only crucial that they be arranged essentially in a plane and pierce essentially parallel to the upper side 3a of the test sample.

Figure 2:
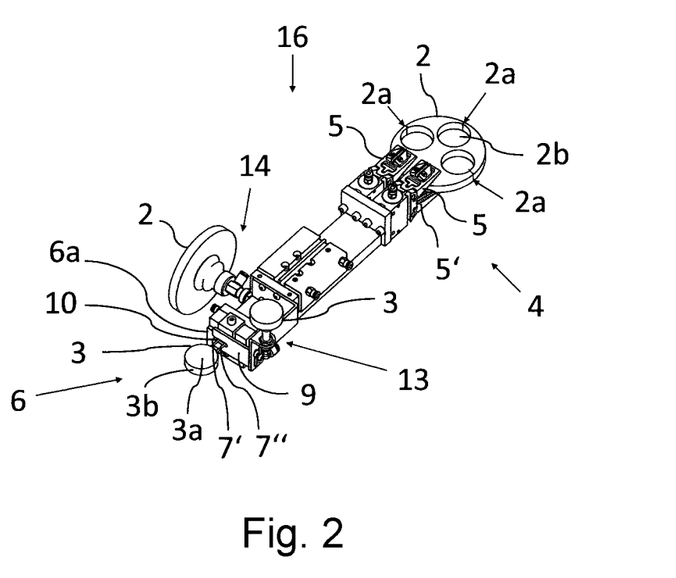
FIG. 2 is the illustration on FIG. 1a, exemplarily with all effectors in an operating state.

FIG. 2 shows the same multifunctional gripper 16 as on FIG. 1, this time for demonstration purposes on all effectors 4, 5, 13, 14 fitted with raw samples 2 and test samples 3. The double gripping jaw pair 5, 5' of the first effector 6 holds a raw sample 2. The latter has three punching areas 2b, from which test samples 3 were punched. An edge cut 2a leads to the outer edge of the raw sample 2 proceeding from each punching area 2b. This edge cut 2a is guided out before the punching process, and used to ensure that the jaw gripper 6 can pull the raw sample 2 around the test sample 3 still being held in the punching device 32 (see FIG. 6a) and out of the punching device 32. High holding forces are required for this purpose, since material and frictional forces must be overcome, so as to achieve an opening of the raw sample 2 around the punched and still fixated test sample 3 along the edge cut 2a. The edge cuts 2a can take place either away one directly after the other for all test samples 3 of a raw sample 2 to be punched, or directly before the respective punching process for each test sample 3 to be punched. This has to do with the handling controller. Further details regarding the above are described for FIG. 6a, 6b.

For punching purposes, the jaw gripper 4 guides the raw sample 2 to the punching device 32 (not shown, see FIG. 6a) and positions it in the punching device 32 in such a way that the punching iron 28 (not shown, see FIG. 6a) hits precisely the end of the end section 2a. The reason why the punching areas 2b do not lie directly in the edge area of a raw sample 2 is that the latter can have damages or irregularities. Punching test samples 3 inside of the raw sample surface ensures that the test samples 3 all have the same quality and quantity.

The two needles 7', 7" of the skewer-type gripper 6 as the second effector 6 carry a test sample 3, whose edge area 3a has been pierced by the needles 7. To this end, the actuator 11 brings the front surface 9 of the stripping device 8 into a position on the base 6a in which the needles 7', 7" protrude through the recess 10 of the front surface. The recess 10 is dimensioned in such a way as to be smaller than the outer contour of the test sample 3, so that the latter is pushed by the needles 7', 7" along with the front surface 9 when the front surface 9 is again moved away from the base 6a by the actuator 11. The same effect is achieved in an alternative configuration not depicted here when the skewer-type means 7 are arranged so that they can enter and exit the base 6a, and the front surface 9 is integrated into the base 6a, so that the test sample is stripped from the front surface 9 as the needles 7', 7" are retracted back into the base 6a through the recess 10. When working with hollow needles and exposure to compressed air, the embodiment described first is simpler to realize, since immovable needles 7', 7" can be more easily pressurized with compressed air.

In particular when using hollow needles, a material suitable for wear resistance must be selected. Hardened stainless steel is suitable for this purpose, for example, wherein the tips of hollow needles are ideally beveled as in the case of injection cannulas, so as to facilitate penetration.

The third effector 13 is a vacuum suction gripper 13 that carries a test sample 3, and the fourth effector is also a vacuum suction gripper 14 that carries a raw sample 2. The suction gripper 14 has larger dimensions than the suction gripper 13, so that a larger holding force can be provided for the larger raw samples.

Figure 3A:
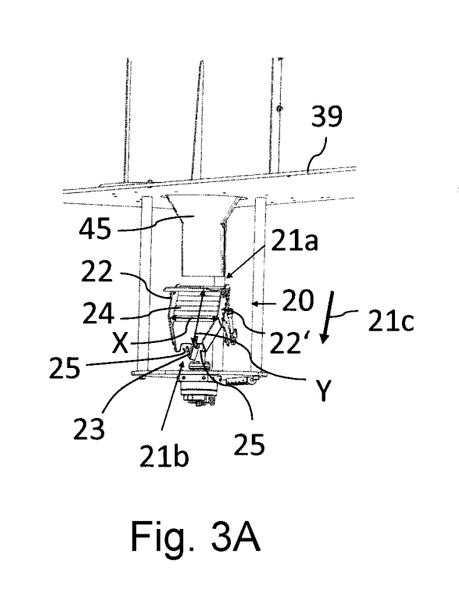
FIG. 3A, 3B is the positioning device according to the invention in an exemplary embodiment.
Figure 3B:
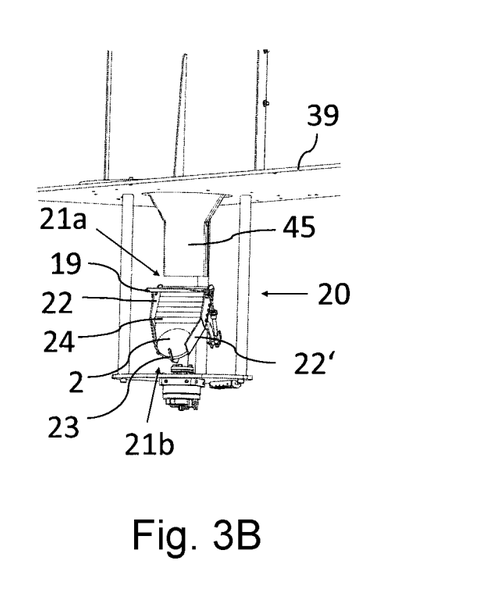

FIGS. 3a and 3b show a positioning device 20 according to the invention in an exemplary embodiment, with which a raw sample 2 can be fed in a defined manner to the handling system 1 according to the invention. Not all described elements are visible or provided with reference numbers in both illustrations. FIG. 3a shows the device without and FIG. 3b with positioned raw sample 2. The positioning device 20 is here connected with a housing 39 (only denoted) that encases the entire test system 30 (not shown), or integrated into the latter, specifically directly underneath the housing cover 39. A feeder 45 serves to feed raw samples 2 to the positioning device 20. Depicted is the sliding surface 21 with a feed side 21a and a deposition side 21b, wherein it has a direction of inclination (arrow) 21c in the longitudinal alignment Y, which a raw sample 2 transferred by a feeder 45 to the receiving side 21a uses to slide over to the deposition side 21b via the sliding surface 21 solely through exposure to the force of gravity. The sliding surface 21 is here formed by the rollers 24 that take up the entire width and are arranged in parallel one behind the other, which are rotatably mounted in the direction of inclination 21c, and thereby facilitate the sliding movement by minimizing the frictional forces. Alternatively, the sliding surface 21 can also be configured as a homogenous surface, but must then be coated, so as to largely avoid the material deposits of sticky raw samples 2 caused by friction during the sliding process. Another configuration for minimizing frictional forces would involve arranging a respective plurality of spaced apart individual rollers one next to the other instead of continuous cylindrical rollers 24, wherein the rollers of a roller series can be arranged linearly with the upstream and downstream rollers, or even offset relative to each other.

In the transverse direction X of the sliding surface 21, side elements 22, 22' ensure that the raw sample 2 does not exit the sliding surface 21 while sliding over it. The arrangement of converging side elements 22, 22' tapers in the direction of inclination 21c. As a result, the raw sample 2 can be positioned in the transverse alignment X while sliding. Since the tapering side elements 22, 22' are symmetrically configured, the raw sample 2 becomes centered, although asymmetry could also provide for other X positions. Catching means 22, 22', 23 are provided for positioning in the longitudinal direction Y. The latter are comprised on the one hand of the edge elements 22, 22' converging toward the direction of inclination 21c. In addition, the hook 23 protruding out of the sliding surface 21 on the deposition side 21 also serves as a catching means. The latter can position the raw sample 2 in the longitudinal alignment Y in conjunction with the edge elements 22, 22', whether given small raw samples alone or larger raw samples 2. The hooks 23 ensure that raw samples 2 of any size are reliably positioned in the longitudinal alignment Y, without requiring that the positioning device be retrofitted, since raw samples 2 can differ significantly in their diameter, as mentioned at the outset. Cavities 25 serve to allow the jaw gripper 4 with its gripping jaws 5, 5' (see FIGS. 1a and 2) unimpeded access from both sides of the raw sample 2, wherein the hook 23 fits into the area of the recess 17 of the jaw gripper 4. A cover device 19 here with an adjustable design is shown in an open position, and in the closed position, while a raw sample 2 is being fed through the feeder 45, ensures that the raw sample 2 cannot exit via the side elements 22, 22', even given an unfavorable impingement. Such a feeder allows the automatic transfer to the test system starting with raw sample removal on the production line. The cut raw samples then need only be brought into the conveying means, so as to automatically get into the feeder to the positioning device.

Figure 4:
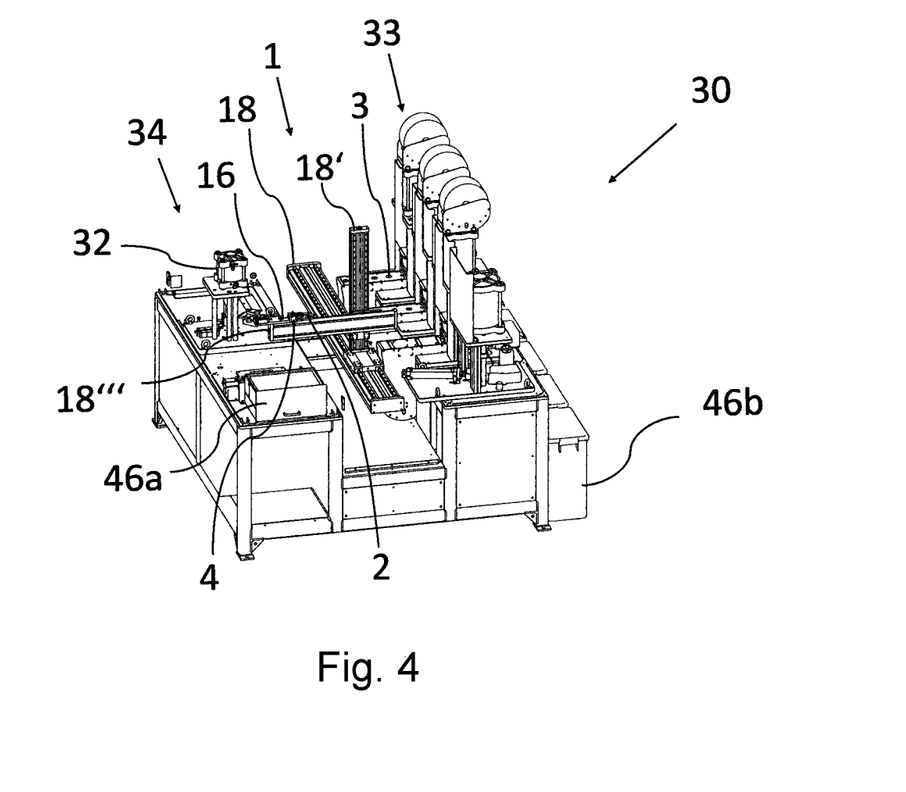
FIG. 4 is the handling system according to the invention in a test system according to the invention in an exemplary embodiment.

FIG. 4 shows the handling device 1 according to the invention in a simple embodiment as a linear system 1 with four axes 18, 18', 18", 18'" in a test system 30 according to the invention with the inventive skewer-type gripper 6 on a multifunctional gripper 16 according to the invention. The handling system 1 is arranged between the working area 34 with punching device 32 and storage containers 46a for processed raw samples 2 and the test unit 33 with storage containers 46b for processed test samples 3 (not shown). The multifunctional gripper 16 according to the invention is arranged on the fourth axis 18'". However, the effectors 4, 5, 13, 14 can just as well each be arranged independently on the fourth axis 18'". Effector 4 on the multifunctional gripper 16 carries a raw sample 2. A controller (not shown) ensures that the axes 18, 18', 18", 18'" of the handling system 1 and the effectors 4, 6, 13, 14 are correspondingly moved, positioned, oriented and exposed to feed force on the fourth axis 18'", so that the processes described both above and further below can be implemented. The first axes 18, 18', 18" are each linearly movable, while the fourth axis 18'" that carries the effectors has four degrees of freedom, so that the effectors are positioned, aligned and exposed to a feed force. The further interaction between elements of the test system 30 will be explained in more detail below in another exemplary embodiment based on FIGS. 5a and 5b.

FIGS. 5a and 5b show the test system 30 according to the invention in another exemplary configuration from two different perspectives. The handling system 1 is here realized as a robot arm 31, which assumes a varying position in the two perspectives. Some of the described elements can only be discerned from one respective perspective, but will be described uniformly here. A working area 34 with a punching device 32 and edge cutting device 37, washing device 38, storage device 35, 36 and storage container 46a for raw samples is arranged opposite the test unit 33 having the individual material testing machines 33' to 33"". This working area 34 is used to receive raw samples 2, if necessary to wash and dry them, introduce edge cuts 2a, punch test samples 3 (not shown) out of them, and feed them to the test unit 33. For this purpose, a robot arm 31 is arranged between the test unit 33 and working area 34 as a handling system 1, and here equipped with a multifunctional gripper 16. See the explanations for FIGS. 1a to 1d and 2 for details about the multifunctional gripper 16.

The storage device 35, 36 has a stationary storage device 35 and a mobile storage device 36. The mobile storage device can be assembled outside of the test system, and introduced into the test system 30 in an assembled state. Both storage devices 35, 36 comprise troughs 35a, 36a. The troughs 35a reveal an elevated edge area 35b that serves as a stripping edge (see also FIG. 6a).

Visible on the robot arm 31 is the multifunctional gripper 16 with a raw sample 2 held in the jaw gripper 4. The test sample 3 is fed to the individual testing machines 33' to 33'''' via a conveyor belt 49, on which the suction gripper 13 as the third effector 13 exactly positions the test sample 3, so that once it reaches the respective testing machine 33' to 33'''', it is there positioned correspondingly to be taken by the machine-integrated transport device (film strip, not shown). As the conveyor belt is moving 47, the test sample 3 is here pushed onto the film strip of the testing machine 33' to 33'''' once reaching its end, and transported further on the latter in the area of the testing machine 33' to 33'''', until it is deposited into a corresponding storage container 46b after the testing process. In the meantime, the next test sample 3 has arrived at the respective testing machine 33' to 33'''', and the next testing process can be immediately performed. Maximum testing efficiency can be achieved through the automated serialization of the testing process for each individual testing machine 33' to 33'''' combined with the simultaneous parallelization of the testing processes in the test unit 33. A controller (not shown) ensures that the robot arm 31 and effectors 4, 6, 13, 14 are correspondingly moved, positioned, oriented and exposed to a feed force, so that the process described above and further below can be implemented.

To ensure the traceability of the archived raw samples, the raw samples can be automatically labeled. The data required for this purpose are prescribed by the controller (not shown). Labeling best takes place after the punching processes have ended, when the raw sample 2 can still be reliably held and correspondingly oriented by the jaw gripper 4.

FIG. 6a shows a working area 34 as a partial area of the test system 30 according to the invention with the storage device 35, 36 according to the invention. Both have correctly formed troughs 35a, 36a, in which the test samples 3 can be positioned for retrieval by the third effector 13 (suction gripper) from the second effector 6 (skewer-type gripper). The exact position of the test samples 3 is important so as to enable an exact receiving and positioned relaying of the test samples 3 to the test unit 33. The third effector 13 configured as a suction gripper 13 can remove test samples 3 from assembled troughs 35a, 36a, and feed them to one of the testing machines 33' to 33'''' of the test unit 33.

The troughs 35a, 36a have elevated edge areas 35b, 36b, which are used for stripping the raw sample 2 from the skewer-type means 7 of the skewer-type gripper (not shown) into the trough 35a, 36a. As an alternative to the stripping device 9, 10 on the skewer-type gripper 6, the stripping edge 3b can be used for stripping skewered test samples 3 (not shown). Notches 35c are here present on the edge of the troughs 35, into which the skewer-type means 7 (not shown) can engage in a correctly fitting manner during the stripping process, so as to simplify stripping. The troughs 35a, 36a can be coated with Teflon to prevent the still sticky test sample 3 from possibly adhering.

The storage device 35 is designed as a stationary intermediate storage, which is immovably installed in the working area 34, and assembled during the regular working progress by the skewer-type gripper 6. The storage device 36 is an optional mobile intermediate storage, which can be supplied to the working area 34 of the test system 30 from outside. The storage device 36 is then assembled outside of the test system 30, so that test samples 3 can be slipped into the automated sequence from outside. The mobile removal and supply is here realized according to the drawer principle, similarly to that of container 46a. However, it must here be ensured that the storage device 36 assumes a defined position inside of the working area, so as to enable a defined transfer of the test sample from the troughs 36 via the third effector 13 here as well.

Located on the left side of the storage device 35, 36 is a container 46a, in which the processed raw samples 2 can be deposited with the fourth effector 14 (not shown) configured as a suction gripper 14 for archiving or disposal purposes. The container 46a can be designed as a drawer that can be opened and removed, so that the raw samples 2 deposited therein can be taken out of the test system 30 from outside. Located to the right of the storage device 35, 36 is a washing device 38. The latter is a basin 38 that can be pressurized with compressed air via nozzles. Washing becomes necessary if release agent is still on the raw sample 2. The release agent is used to diminish adhesion during the handling process in the first hot phase. To this end, the raw sample 2 is first completely held by the first effector 4 in the basin 38, in which washing liquid is either already present, or the raw sample 2 is then completely wetted by water nozzles. The raw sample 2 must here be uniformly exposed to the water, since it simultaneously has a cooling effect, and cannot irregularly affect the raw sample 2. After washed, the raw sample 2 is vertically aligned to prevent the limp raw sample 2 from kinking. The raw sample 2 is then dried with compressed air.

Located rightmost in the working area 34 is a punching device 32, and at an inclination thereunder an edge cutting device 37, whose interaction with the test system 30 is explained in more detail on FIG. 6b.

FIG. 6b shows a punching device 32 and an edge cutting device 37 from prior art as a detail to FIG. 6a. The purpose of explaining these devices is to explain the function of the first effector 4 and the forces acting on the raw sample 2 in more detail. The edge cutting device 37 is used to introduce an edge cut 2a (see FIG. 2) in the raw sample 2 (not shown) for each punching area 2b (see FIG. 2). In order to attach the end sections, the first effector 4 holds the raw sample 2 in the working area of the edge cutting device, inside of which a blade travels from below through the raw sample 2. For this purpose, the raw sample 2 must be exactly positioned in such a way that the respective edge cut 2a reaches precisely up to the punching area 2b. The system can here be controlled in such a way that, after each edge cut 2a is completed, the raw sample 2 is brought into the punching device 32 for punching the respective test sample 3, or all required edge cuts 2a can initially be attached, after which the punching processes can be subsequently performed for all test samples 3 from a raw sample 2. This avoids unnecessary movements of the handling system 1 (not shown). If all edge cuts 2a are introduced one after the other, the raw sample 2 must be turned to the next edge cutting position by the jaw gripper 4 over the blade 37a after each cutting process.

The punching device 32, here a volume punch 32, has a fixed plunger 27 on which the raw sample 2 is to be positioned by the jaw gripper 4 with punching area 2a. The compression plunger 26 is used to immobilize the punching area 2a through compression, and to define the volume while cutting with the punching iron 28. The punching iron 28 is guided through the raw sample 2 from below along the immobile plunger 27. The jaw gripper 4 then exerts a tensile force on the raw sample 2 still fixed in place with the compression plunger. The raw sample 2 thereby opens around the punching area 2b in the area of the edge cut 2a, so that the jaw gripper 4 can remove the raw sample 2 around the punching area 2b now comprising the test sample 3 from the punching device 32.

In the next step, the second effector 6 (not shown) can securely skewer the still compressed test sample 3 with the skewer-type means 7, and in the process move it into a defined position on the skewer-type means 7 (see FIG. 2). As soon as the test sample 3 has been securely received by the skewer-type gripper 6, the compression plunger 26 opens, and the skewer-type gripper can lift up the test sample 3. The holding force of the skewer-type gripper 6 is sufficient to overcome the adhesive force of the test sample 6 on the surface of the plunger 27. In the case of a conventional punch (not shown) having no compression plunger 26, a punching iron travels from above into the raw sample. When the punching iron is lifted up again, the test sample remains stuck in the punching iron, and is pushed downwardly toward the deposition surface out of the punching iron by an ejector guided inside of the punching iron. In order to receive the test sample 3 with the skewer-type gripper 6, the test sample 3 can be held against the deposition surface by the ejector, or the skewer-type gripper 6 can skewer the test sample against an abutment that holds the test sample in its position against the skewering direction.

The received test sample 3 can be stripped from the skewer-type gripper 6 into a trough 35a of the storage device 35. Depending on the dimensions, up to five test samples 3 can be punched out of a raw sample 2.

Figure 7:
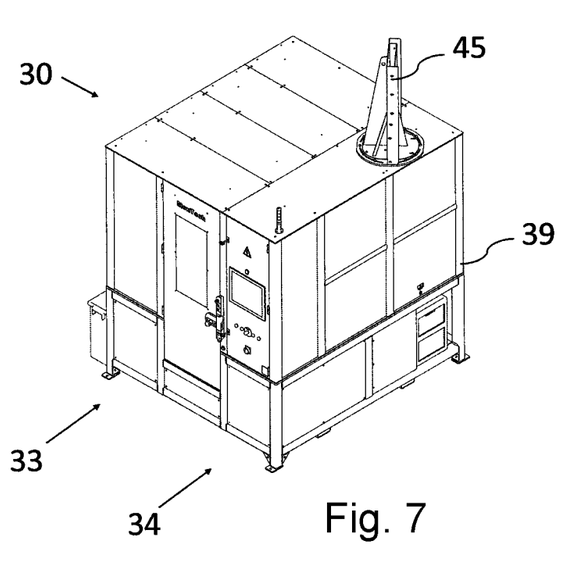
FIG. 7 is the test system according to the invention in an embodiment variant.

FIG. 7 shows an outer view of a test cell 30. The test system 30 with the working area 34 and test unit 33 is encased by a housing 39 that can be sealed airtight, so that it can be pressurized with overpressure, which serves to protect against penetrating dust particles. The raw samples 2 are fed into the positioning device 20 (not shown) arranged below the housing roof (corresponding to FIG. 3a, 3b) via the feeder 45, here depicted as an infeed hopper 45 that can be fitted via a conveyor belt (not shown). Such a test cell 30 can be arranged directly in the production area, i.e., in proximity to a production line, without there arising any danger of contamination or fluctuating test conditions. If the samples are removed immediately after the mixing process, the time window until the test is minimized. This enables the fastest possible feedback of test results, in particular if the controller of the test system 30 according to the invention is coupled with that of the production line. If the raw samples are only taken after a certain cooling line, the stickiness of the material diminishes, which lowers the danger of deposits caused by abrasion, in particular of the freshly removed raw samples 2. The temperatures at the removal sites depend on the system speed, and can vary between room temperature and 100° C.

The figures only show exemplary embodiments. The handling system 1 as well as the test system 30 can also be put together differently than depicted on the figures and claimed. Depending on how a material test is specifically conceived, working steps can be excluded from the automated process or otherwise handled, so that the first 4, third 13 and/or fourth 14 effector become unnecessary, and thus do not absolutely have to be part of the handling system 1 according to the invention. The positioning device 20 can also be integrated into the handling system 1. The crucial factor is that the skewer-type gripper 6 according to the invention enable the controlled, automated handling of test samples 3 in material tests.

LIST OF REFERENCE NUMERALS

1 Handling system
2 Raw sample
2a Edge cut
2b Punching area, punched area
3 Test sample
3a Upper side
3b Edge area
4 First effector, jaw gripper
5, 5' Gripping jaw
5a Fluting
6 Second effector, skewer-type gripper
6a Base
7 Skewer-type means
7', 7", 7''', Needle, hollow needle
7a Rib
9 Front surface
10 Recess
11 Connecting element
12 Arrow: Directions of movement
13 Third effector, suction gripper
14 Fourth effector, suction gripper
16 Multifunctional gripper
17 Recess
20 Positioning device
20 Sliding surface
21a Feed side
21b Deposition side
21c Arrow: Direction of inclination
22, 22' Side elements
23 Hook
24 Rollers
25 Cavities
26 Compression plunger
27 Fixed plunger
28 Punching iron
29 Conveying means, conveyor belt
30 Test system, test cell
31 Robot arm
32 Punching device
33 Test unit
33', 33", 33''', 33'''' Material testing machines
34 Working area
35, 36 Storage device
35a, 36a Trough
35b, 36b Stripping edge
35c Notch
37 Edge cutting device
37a Blade
38 Washing device
39 Housing
45 Feeder
46a, 46b (Storage) container
47 Conveying means, conveyor belt
X Transverse alignment
Y Longitudinal alignment

The invention claimed is:

1. A multifunctional gripper (16) for a robot arm (31), comprising:
a first effector (4) with gripping jaws (5, 5') that are moved toward each other in pairs for receiving and handling, by moving, positioning and securing, a raw sample (2) before and while punching a test sample (3), a second effector (6) with a skewer-type gripper (6) for receiving and handling by transferring the test sample (3) after punching, wherein the skewer-type gripper (6) is configured for one-sidedly receiving the test sample (3) positioned in a defined manner and still compressed by plungers (26, 27) in a punching device (32), the test sample consisting of sticky viscoelastic materials of up to 100° C. and having an upper side (3a) and an edge area (3b) of 5 to 18 mm, wherein the gripper (6) has a base (6a) and at least one skewer (7, 7',7", 7''') with an expansion arranged in a single plane therein, said at least one skewer being configured to pierce into the edge area (3b) of the still compressed test sample (3) with the plane of expansion parallel to the upper side (3a), wherein the gripper (6) is configured and set up for horizontally receiving the test sample (3) from the punching device (32), and the gripper (6) is exposed to a feed force of up to eight kilograms, wherein the skewer is a hollow needle pressurized with compressed air, a third effector (13) with a suction gripper for handling, by transferring and positioning, the test sample (3), a fourth effector (14) with a suction gripper for handling by transferring the raw sample (2), wherein each of the effectors (4, 6, 13, 14) is arranged and designed so that it is controlled in terms of its position, its position relative to the raw sample (2) or test sample (3), its alignment, contact force and movement.

2. The multifunctional gripper (16) according to claim 1, characterized in that each of the gripping jaws (5, 5') has a marginal recess (17) in its gripping range, and is thereby divided at least partially in two.

* * * * *